(12) United States Patent
McGee et al.

(10) Patent No.: US 8,534,031 B2
(45) Date of Patent: Sep. 17, 2013

(54) PACKAGING SOLUTIONS

(75) Inventors: Joseph A. McGee, Canandaigua, NY (US); David Paul Vanderbilt, Webster, NY (US); Paul L. Valint, Jr., Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 712 days.

(21) Appl. No.: 12/641,483

(22) Filed: Dec. 18, 2009

(65) Prior Publication Data

US 2010/0162663 A1    Jul. 1, 2010

Related U.S. Application Data

(60) Provisional application No. 61/203,884, filed on Dec. 30, 2008.

(51) Int. Cl.
*B65B 55/18* (2006.01)

(52) U.S. Cl.
USPC .............................................. 53/431; 422/28

(58) Field of Classification Search
USPC .............. 53/425, 431, 471; 206/5.1; 422/25, 422/28, 40
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deicherte et al. | |
| 4,197,266 A | 4/1980 | Clark et al. | |
| 4,304,705 A | 12/1981 | Heilman et al. | |
| 4,378,411 A | 3/1983 | Heilman et al. | |
| 4,485,236 A | 11/1984 | Rasmussen et al. | |
| 4,555,732 A | 11/1985 | Tuhro | |
| 4,695,608 A | 9/1987 | Engler et al. | |
| 4,740,533 A | 4/1988 | Su et al. | |
| 4,786,436 A | 11/1988 | Ogunbiyi et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,081,197 A | 1/1992 | Heilmann et al. | |
| 5,089,578 A | 2/1992 | Valint, Jr. et al. | |
| 5,177,165 A | 1/1993 | Valint, Jr. et al. | |
| 5,209,865 A | 5/1993 | Winterton et al. | |
| 5,219,965 A | 6/1993 | Valint, Jr. | |
| 5,260,000 A | 11/1993 | Wandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 6,440,366 B1 | 8/2002 | Salpekar et al. | |
| 6,858,310 B2 | 2/2005 | McGee et al. | |
| 7,837,934 B2 * | 11/2010 | Linhardt et al. | 422/28 |
| 8,109,064 B2 * | 2/2012 | Glasbey et al. | 53/431 |
| 8,247,461 B2 * | 8/2012 | Smith et al. | 516/204 |
| 2003/0125498 A1 * | 7/2003 | McCabe et al. | 528/25 |
| 2007/0037897 A1 * | 2/2007 | Wang et al. | 523/106 |
| 2007/0116740 A1 * | 5/2007 | Valint et al. | 424/428 |
| 2007/0163210 A1 * | 7/2007 | Glasbey et al. | 53/425 |
| 2008/0110770 A1 * | 5/2008 | Burke et al. | 206/5.1 |
| 2008/0141628 A1 * | 6/2008 | Lang et al. | 53/431 |
| 2008/0148689 A1 * | 6/2008 | Xia et al. | 53/431 |
| 2008/0151180 A1 | 6/2008 | Vanderbilt et al. | |
| 2008/0307751 A1 * | 12/2008 | Newman et al. | 53/425 |

FOREIGN PATENT DOCUMENTS

| | | |
|---|---|---|
| EP | 0 392 735 | 7/1996 |
| WO | WO 96/31792 | 10/1996 |
| WO | WO99/10022 | 3/1999 |
| WO | WO2008/079495 | 7/2008 |

OTHER PUBLICATIONS

Dicesare, N. et al. "Spectral Properties of Fluorophores . . . " J of Phys. Chem., vol. 105, Jul. 2001, pp. 6834-6840.
Lai, Yu-Chin, "The Role of Bulky Polysiloxanylalkyl Methacrylates in Polyurethane-Polysiloxane Hydrogels," Journal of Applied Polymer Science, vol. 60, 1193-1199 (1996).
Odian, *Principles of Polymerization*, 2nd Ed., John Wiley & Sons, p. 425-430 (1981).

* cited by examiner

*Primary Examiner* — Alexandra Elve
*Assistant Examiner* — Eyamindae Jallow
(74) *Attorney, Agent, or Firm* — Glenn D. Smith

(57) ABSTRACT

Packaging systems for storing ophthalmic devices such as contact lenses and to methods for packaging such ophthalmic devices with solutions to improve the comfort of the lenses during wear are disclosed.

4 Claims, No Drawings

PACKAGING SOLUTIONS

This application claims the benefit of Provisional Patent Application No. 61/203,884 filed Dec. 30, 2008 which is incorporated by reference herein.

BACKGROUND OF THE INVENTION

1. Technical Field

The present invention generally relates to packaging solutions for ophthalmic devices such as contact lenses.

2. Description of Related Art

Blister-packs and glass vials are typically used to individually package each soft contact lens for sale to a customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking.

It has been stated that if a lens is thoroughly cleaned before insertion, lacrimal fluid can adequately wet the lens. Furthermore, the difficulties of adding a surfactant to a packaging solution, including the possibility of lowering shelf-life and/or adverse reactions during heat sterilization, have further limited the use of surfactants in a packaging solution for the purpose of providing any possible or marginal effect on lens comfort. It is only after a lens has been worn, when proteins or other deposits have formed on the surface of the lens, that surfactants have been used in standard lens-care solutions.

It is highly desirable that contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

Poloxamine and poloxamers are examples of non-ionic surfactants having one or more poly(oxyalkylene) chains. Poloxamines and poloxamers are well-known wetting and lubricating agents for contact lenses and have been used in lens wetting drops and in lens-care solutions for treating lenses after use or while in use in the eye. For example, U.S. Pat. No. 4,786,436 disclose poloxamine as a wetting agent. Contact-lens rewetting drops containing surfactants such as poloxamine and poloxamer have been used to make contact lens wear more comfortable, to soothe the eyes, and to moisten lenses to minimize dryness. Surfactants such as poloxamine, poloxamer, and tyloxapol have been used in multi-purpose solutions, for cleaning, wetting, and storing lenses.

Certain combinations of poly(oxyalkylene) surfactants have also been disclosed for use in the eye to preventively clean lenses and inhibit deposits. For example, U.S. Pat. No. 5,209,865 discloses the combination of certain poloxamers and poloxamines to maintain clean lenses in the eye.

U.S. Pat. No. 6,440,366 ("the '366 patent") discloses a package containing a contact lens suitable for immediate use which comprises (a) a solution comprising a non-ionic surfactant that is a compound comprising at least 90 weight percent of poly(oxyethylene) and poly(oxypropylene) segments, in one or more block copolymer chains, and (b) an effective amount of a tonicity adjusting agent such that the solution has an osmolality of 200 to 400 mOsm/kg; wherein the solution has a pH of about 6 to 8 and is heat sterilized and lacks an effective disinfecting amount of a disinfecting agent. The '366 patent further discloses that the surfactant is a poly(oxypropylene)-poly(oxyethylene) adduct of ethylene diamine.

It would be desirable to provide an improved packaging system for ophthalmic devices such as a contact lens such that the lens would be comfortable to wear in actual use and allow for extended wear of the lens without irritation or other adverse effects to the cornea.

SUMMARY OF THE INVENTION

In accordance with one embodiment of the present invention, a method of preparing a package comprising a storable, sterile ophthalmic device is provided comprising:

(a) providing an ophthalmic device obtained from a polymerization product of a monomeric mixture comprising (i) a polymerizable monomer containing a boronic acid moiety and an electron withdrawing moiety; and (ii) an ophthalmic device-forming comonomer;

(b) immersing the ophthalmic device in an aqueous packaging solution comprising a hydrophilic reactive polymer having complementary reactive functionalities along the polymer chain, wherein the solution has an osmolality of at least about 200 mOsm/kg and a pH in the range of about 6 to about 9;

(c) packaging the solution and the ophthalmic device in a manner preventing contamination of the device by microorganisms; and (d) sterilizing the packaged solution and ophthalmic device.

In accordance with a second embodiment of the present invention, a packaging system for the storage of an ophthalmic device is provided comprising a sealed container containing one or more unused ophthalmic devices obtained from a polymerization product of a monomeric mixture comprising (i) a polymerizable monomer containing a boronic acid moiety and an electron withdrawing moiety; and (ii) an ophthalmic device-forming comonomer and immersed in an aqueous packaging solution comprising a hydrophilic reactive polymer having complementary reactive functionalities along the polymer chain, wherein the solution has an osmolality of at least about 200 mOsm/kg, a pH of about 6 to about 9 and is heat sterilized.

In accordance with a third embodiment of the present invention, a packaging system for the storage of an ophthalmic device is provided comprising:

(a) an aqueous packaging solution comprising a hydrophilic reactive polymer having complementary reactive functionalities along the polymer chain, wherein the solution has an osmolality of at least about 200 mOsm/kg and a pH in the range of about 6 to about 9;

(b) at least one ophthalmic device obtained from a polymerization product of a monomeric mixture comprising (i) a polymerizable monomer containing a boronic acid moiety and an electron withdrawing moiety; and (ii) an ophthalmic device-forming comonomer; and (c) a container for holding the solution and ophthalmic device sufficient to preserve the sterility of the solution and ophthalmic device, wherein the solution does not contain an effective disinfecting amount of a disinfecting agent.

The aqueous packaging solutions of the present invention containing at least a hydrophilic reactive polymer having complementary reactive functionalities along the polymer chain is believed to provide a more uniform coating on the surface of an ophthalmic device obtained from a polymerization product of a monomeric mixture comprising (a) a polymerizable monomer containing a boronic acid moiety and an electron withdrawing moiety; and (b) an ophthalmic device-forming comonomer thereby resulting in improved lubricity and/or wettability of the lens. Thus, the lens will be more comfortable to wear in actual use and allow for extended wear of the lens without irritation or other adverse effects to the cornea.

DETAILED DESCRIPTION OF THE PREFERRED EMBODIMENTS

The present invention provides a packaging system for the storage of ophthalmic devices intended for direct contact with body tissue or body fluid. As used herein, the term "ophthalmic device" refers to devices that reside in or on the eye. These lenses can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. Any material known to produce an ophthalmic device including a contact lens can be used herein.

The ophthalmic devices are formed from a polymerization product of (a) a polymerizable monomer containing a boronic acid moiety and an electron withdrawing moiety; and (b) an ophthalmic device-forming comonomer. Suitable polymerizable monomers containing a boronic acid moiety and an electron withdrawing moiety for use in forming the ophthalmic devices of the present invention include boronic acid-containing monomers having one or more polymerizable ethylenically unsaturated-containing radicals attached thereto. Representative examples of a "polymerizable ethylenically unsaturated-containing radical" include, by way of example, (meth)acrylate-containing radicals, (meth)acrylamido-containing radicals, vinylcarbonate-containing radicals, vinylcarbamate-containing radicals, styrene-containing radicals, itaconate-containing radicals, vinyl-containing radicals, vinyloxy-containing radicals, fumarate-containing radicals, maleimide-containing radicals, vinylsulfonyl radicals and the like. As used herein, the term "(meth)" denotes an optional methyl substituent. Thus, for example, terms such as "(meth)acrylate" denotes either methacrylate or acrylate, and "(meth)acrylamide" denotes either methacrylamide or acrylamide.

In one embodiment, a polymerizable ethylenically unsaturated radical can be represented by the general formula:

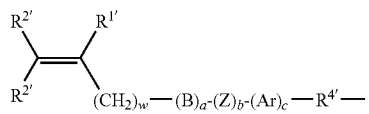

wherein $R^{1'}$ is hydrogen or a alkyl group having 1 to 6 carbon atoms such as methyl; each $R^{2'}$ is independently hydrogen, an alkyl radical having 1 to 6 carbon atoms, or a —CO—Y—$R^{5'}$ radical wherein Y is —O—, —S— or —NH— and $R^5$ is an alkyl radical having 1 to about 10 carbon atoms; $R^{4'}$ is a linking group (e.g., a divalent alkenyl radical having 1 to about 12 carbon atoms); B denotes —O— or —NH—; Z denotes —CO—, —OCO— or —COO—; Ar denotes an aromatic radical having 6 to about 30 carbon atoms; w is 0 to 6; a is 0 or 1; b is 0 or 1; and c is 0 or 1. The polymerizable ethylenically unsaturated-containing radicals can be attached to the boronic acid-containing monomers having an electron withdrawing moiety as pendent groups, terminal groups or both.

As used herein, the term "electron withdrawing moiety" refers to a group which has a greater electron withdrawing effect than hydrogen. A variety of electron-withdrawing moieties are known and include, by way of example, halogens (e.g., fluoro, chloro, bromo, and iodo groups), $NO_2$, $NR_3^+$, CN, COOH(R), $CF_3$, and the like. The pH of the boronic acid-containing monomer can be adjusted by placing the electron withdrawing moiety in, e.g., a position meta to the boronic acid moiety on the phenyl ring.

Representative examples of suitable polymerizable monomers containing a boronic acid moiety and an electron withdrawing moiety include polymerizable ethylenically unsaturated alkyl boronic acids having an electron withdrawing moiety; polymerizable ethylenically unsaturated cycloalkyl boronic acids having an electron withdrawing moiety; polymerizable ethylenically unsaturated aryl boronic acids having an electron withdrawing moiety and the like and mixtures thereof. Preferred boronic acid polymerizable monomers are derived from 3-vinylphenylboronic acid or 3-methacrylamidophenylboronic acid.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl(isopropyl), n-butyl, n-pentyl, etc., and the like.

Representative examples of cycloalkyl groups for use herein include, by way of example, a substituted or unsubstituted non-aromatic mono or multicyclic ring system of about 3 to about 24 carbon atoms such as, for example, cyclopropyl, cyclobutyl, cyclopentyl, cyclohexyl, perhydronapththyl, adamantyl and norbornyl groups bridged cyclic group or spriro-bicyclic groups, e.g., sprio-(4, 4)-non-2-yl and the like, optionally containing one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

In one embodiment, a polymerizable monomer containing a boronic acid moiety and an electron withdrawing moiety is represented by the general formula:

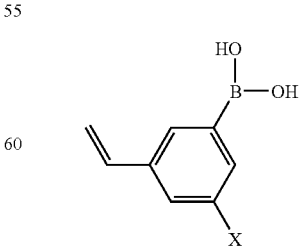

wherein X is an electron withdrawing group such as —$CF_3$, —$NO_2$, —F, —Cl or —Br.

The polymerizable monomers containing a boronic acid moiety and an electron withdrawing moiety can be prepared by the general reaction sequences set forth in Schemes I and II below:

SCHEME I

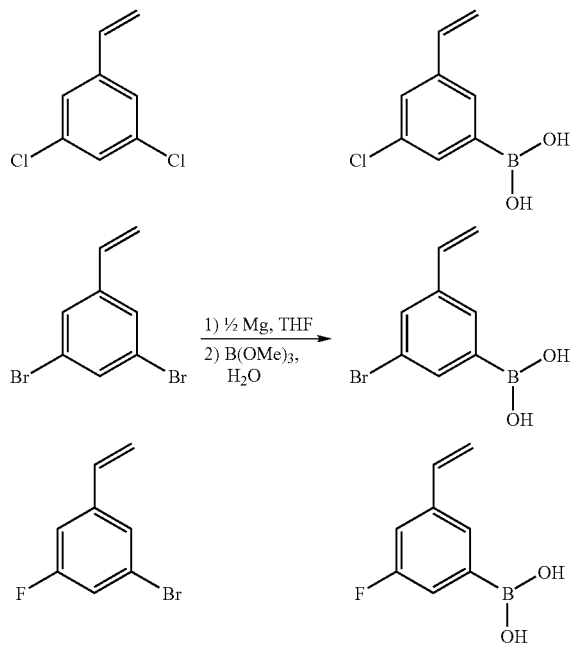

SCHEME II

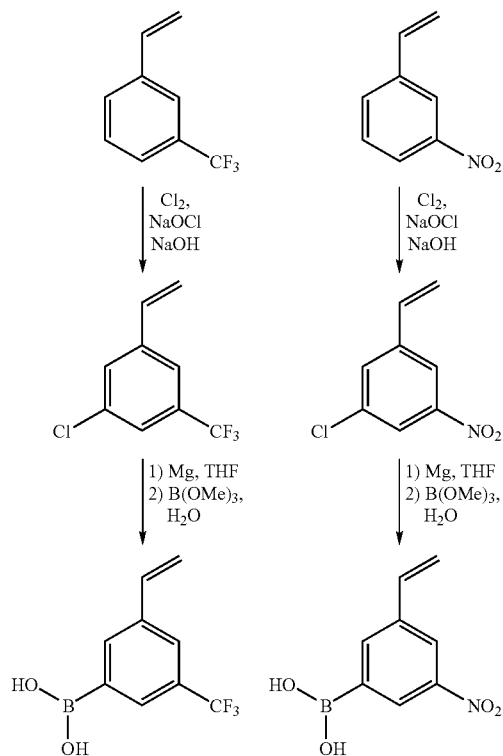

In addition to the polymerizable monomer containing a boronic acid moiety and an electron withdrawing moiety, the monomeric mixture will further contain one or more ophthalmic device-forming comonomers. Generally, the ophthalmic device-forming comonomer contains at least one polymerizable group. In one embodiment, the ophthalmic device-forming comonomer is an ophthalmic device-forming comonomer such as a contact lens-forming comonomer. In another embodiment, the ophthalmic device-forming comonomer is a hydrogel lens forming-containing monomer. Hydrogels comprise a hydrated, cross-linked polymeric system containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer.

Either the silicone-containing monomer or the hydrophilic monomer may function as a crosslinking agent (a crosslinking agent being defined as a monomer having multiple polymerizable functionalities), or alternately, a separate crosslinking agent may be employed in the initial monomer mixture from which the hydrogel copolymer is formed. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) Silicone hydrogels typically have a water content between about 10 to about 80 weight percent.

Applicable silicone-containing monomers for use in the formation of contact lenses such as silicone hydrogels are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth)acrylic monomer is represented by the structure of Formula I:

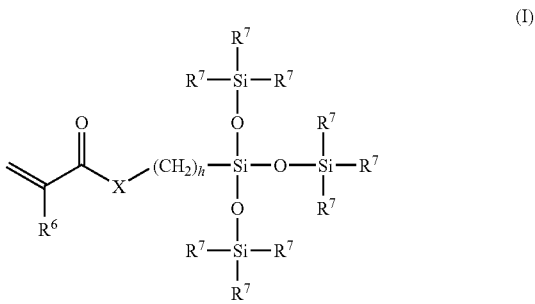

(I)

wherein X denotes —O— or —NR— wherein R denotes hydrogen or a $C_1$-$C_4$ alkyl; each $R^6$ independently denotes hydrogen or methyl; each $R^7$ independently denotes a lower alkyl radical, phenyl radical or a group represented by

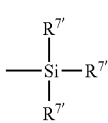

wherein each R⁷' independently denotes a lower alkyl or phenyl radical; and h is 1 to 10.

Representative examples of other applicable silicon-containing monomers includes, but are not limited to, bulky polysiloxanylalkyl carbamate monomers as generally depicted in Formula Ia:

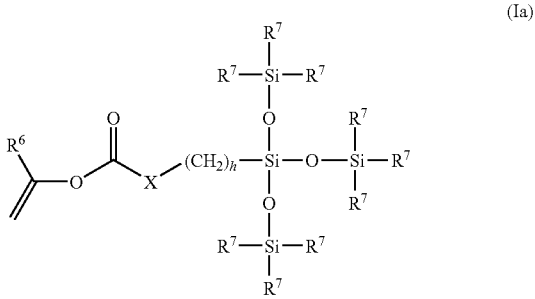

wherein X denotes —NR—; wherein R denotes hydrogen or a $C_1$-$C_4$ alkyl; $R^6$ denotes hydrogen or methyl; each $R^7$ independently denotes a lower alkyl radical, phenyl radical or a group represented by

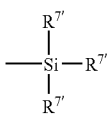

wherein each $R^{7'}$ independently denotes a lower alkyl or phenyl radical; and h is 1 to 10, and the like.

Examples of bulky monomers are 3-methacryloyloxypropyltris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyldisiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety of publications, including Lai, Yu-Chin, "The Role of Bulky Polysiloxanylalkyl Methacryates in Polyurethane-Polysiloxane Hydrogels," *Journal of Applied Polymer Science*, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A denotes a divalent polymeric radical of Formula IV:

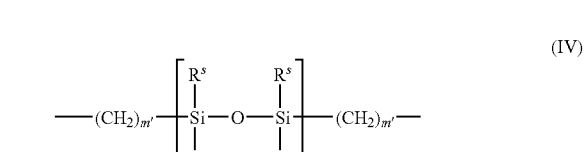

wherein each $R^S$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

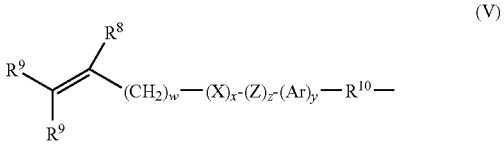

wherein: $R^8$ is hydrogen or methyl;

$R^9$ is independently hydrogen, an alkyl radical having 1 to 6 carbon atoms, or a —CO—Y—$R^{11}$ radical wherein Y is —O—, —S— or —NH—;

$R^{10}$ is a divalent alkylene radical having 1 to about 10 carbon atoms;

$R^{11}$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

A preferred silicone-containing urethane monomer is represented by Formula VI:

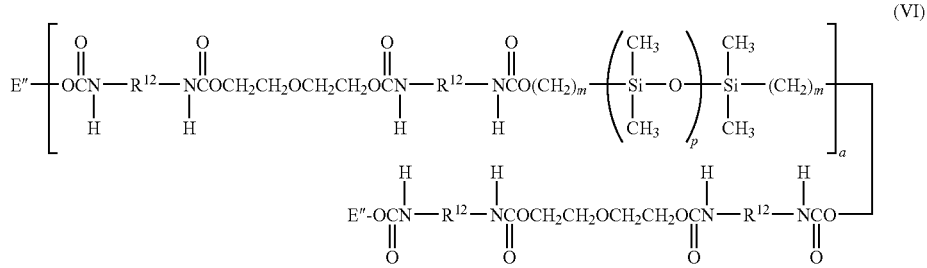

wherein m is at least 1 and is preferably 3 or 4, a is at least 1 and preferably is 1, p is a number which provides a moiety weight of about 400 to about 10,000 and is preferably at least about 30, $R^{12}$ is a diradical of a diisocyanate after removal of the isocyanate group, such as the diradical of isophorone diisocyanate, and each E" is a group represented by:

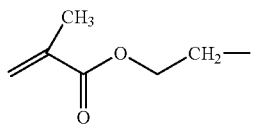

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954,587; 5,010,141 and 5,079,319. The use of silicone-containing monomers having certain fluorinated side groups, i.e., —($CF_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming ophthalmic devices according to the present invention and have been disclosed in various publications and are being continuously developed for use in contact lenses and other ophthalmic devices can also be used. For example, an ophthalmic device-forming comonomer can be a cationic monomer such as cationic silicone-containing monomer or cationic fluorinated silicone-containing monomers.

The monomer mixtures can also contain one or more hydrophilic monomers. Suitable hydrophilic monomers include one or more unsaturated carboxylic acids, vinyl lactams, amides, polymerizable amines, vinyl carbonates, vinyl carbamates, oxazolone monomers, and the like and mixtures thereof. Useful unsaturated carboxylic acids include methacrylic acid or acrylic acid. Useful amides include acrylamides such as N,N-dimethylacrylamide and N,N-dimethylmethacrylamide. Useful vinyl lactams include cyclic lactams such as N-vinyl-2-pyrrolidone. Examples of other hydrophilic monomers include poly(alkene glycols) functionalized with polymerizable groups. Examples of useful functionalized poly(alkene glycols) include poly(diethylene glycols) of varying chain length containing monomethacrylate or dimethacrylate end caps. In a preferred embodiment, the poly (alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the monomeric mixtures in an amount ranging from 0 to about 70 weight percent, based on the total weight of the mixture.

The monomer mixtures can also contain one or more hydrophobic monomers. Suitable hydrophobic monomers include $C_1$-$C_{20}$ alkyl and $C_3$-$C_{20}$ cycloalkyl(meth)acrylates, substituted and unsubstituted $C_6$-$C_{30}$ aryl(meth)acrylates, (meth)acrylonitriles, fluorinated alkyl methacrylates, long-chain acrylamides such as octyl acrylamide, and the like. The hydrophobic monomers can be present in the monomeric mixtures in an amount ranging from 0 to about 30 weight percent, based on the total weight of the mixture.

The monomer mixtures can also contain one or more crosslinking monomers. The crosslinking monomer may be a material having multiple polymerizable functionalities, preferably vinyl functionalities. Representative examples of crosslinking monomers include divinylbenzene; allyl methacrylate; ethyleneglycol di(meth)acrylate, tetraethyleneglycol di(meth)acrylate, polyethyleneglycol di(meth)acrylate; vinylcarbonate derivatives of the glycol di(meth)acrylates and the like. The crosslinking monomers can be present in the monomeric mixtures in an amount ranging from 0 to about 40 weight percent, based on the total weight of the mixture.

In order to prepare the biomedical devices of the present invention that are capable of complexation with coating polymers such as a hydrophilic polymer, it is necessary that the boronic acid groups are present at the surface of the device and are capable of forming complexes with suitable coating polymers at physiological pH (e.g. a pH of about 6.8 to about 7.6). Concentration of the boronic acid groups at the surface of the biomedical device can be accomplished by providing a mold surface that is capable of complexation with boronic acid groups. A mold surface having any of the following functional groups are capable of complexation with boronic acid groups: 1,2 diols, 1,3 diols, dicarboxylic acids, α-hydroxy carboxylic acids and the like. Representative examples of suitable mold materials are ethyl vinyl alcohol resin, poly (ethylene-co-vinyl alcohol), air-plasma oxidized polypropylene and the like.

To meet the pKa requirement, boronic acid groups such as aryl boronic acids are commonly copolymerized with tertiary amines so that some of the amine groups are placed adjacent to the boronic acid groups to interact with the boronic acid groups and lower the effective pKa of the boronic acid to the about 6.8 to about 7.6 range. However, the addition of a polymerizable tertiary amine to a contact lens formulation at a low concentration is generally not desirable because the probability of forming boronic acid-tertiary amine dimer sequences is relatively low. The present invention advantageously employs boronic acid monomers having an electron withdrawing substituent to obviate the need to incorporate a tertiary amine into, for example, a lens formulation, while being able to meet the pKa requirement and allow the boronic acid groups to be present at the surface of the lens.

If desired, the monomer mixtures can also contain a monomer having a tertiary-amine moiety such that the boronic acid moieties on the surface of the ophthalmic device are physiologically acceptable, i.e., a pH value of about 6.8 to about 7.6 (physiological pH values). Examples of monomers copolymerizable with the boronic acid monomer are ethylenically unsaturated monomers containing the tertiary-amine moiety. Specific examples include: 2-(N,N-dimethyl)ethylamino (meth)acrylate, N-[2-(dimethylamino)ethyl](meth)acrylamide, N-[(3-dimethylamino)propyl](meth)acrylate, N-[3-dimethylamino)propyl]meth)acrylamide and vinylbenzyl-N, N-dimethylamine.

The ophthalmic devices of the present invention, e.g., contact lenses or intraocular lenses, can be prepared by polymerizing the foregoing monomeric mixtures to form a product that can be subsequently formed into the appropriate shape by, for example, lathing, injection molding, compression molding, cutting and the like. For example, in producing contact lenses, the initial monomeric mixture may be polymerized in tubes to provide rod-shaped articles, which are then cut into buttons. The buttons may then be lathed into contact lenses.

Alternately, the contact lenses may be cast directly in molds, e.g., polypropylene molds, from the monomeric mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the monomeric mixture between two mold sections, one mold section shaped to form the anterior lens surface and the other mold section shaped to form the posterior lens surface, and curing the monomeric mixture while retained in the mold assembly to form a lens, for example, by free radical polymerization of the monomeric mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetal peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the monomeric mixture at a concentration of about 0.01 to 1 percent by weight of the total mixture.

Polymerization of the mixtures will yield a polymer, that when hydrated, forms a hydrogel. Generally, the mixture will contain the polymerizable monomer having one or more boronic acid moieties in an amount ranging from about 0.1 to about 10 weight percent, and preferably from about 0.5 to about 2 weight percent, based on the total weight of the mixture, and the ophthalmic device-forming comonomer in an amount ranging from about 5 to about 90 weight percent and preferably from about 20 to about 60 weight percent, based on the total weight of the mixture.

When producing a hydrogel lens, the mixture may further include at least a diluent that is ultimately replaced with water when the polymerization product is hydrated to form a hydrogel. Generally, the water content of the hydrogel is greater than about 5 weight percent and more commonly between about 10 to about 80 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

As previously stated, the ophthalmic devices of the present invention, such as a contact lens, should have a sufficient amount of concentrated boronic acid on the surface to provide enhanced wettability and/or lubriciousness to the lens. One manner to accomplish this is to cast the monomer mix in an appropriate mold resin such as an ethyl vinyl alcohol resin and then wet release of the lens from the mold. Another manner is to incorporate the boronic acid-containing monomer into a surface active monomer, see, e.g., U.S. Pat. Nos. 5,117,165 and 5,219,965.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

The ophthalmic device such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

Next, the ophthalmic device will be immersed in an aqueous packaging solution and stored in a packaging system according to the present invention. Generally, a packaging system for the storage of the ophthalmic device according to the present invention includes at least a sealed container containing one or more unused ophthalmic devices as described hereinabove immersed in an aqueous packaging solution. Preferably, the sealed container is a hermetically sealed blister-pack, in which a concave well containing the ophthalmic device is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

In general, the aqueous packaging solution will contain at least a hydrophilic reactive polymer having complementary reactive functionalities along the polymer chain. In one embodiment, the hydrophilic reactive polymer can be monomeric units containing 1,2- or 1,3-diols along the backbone of the polymer chain, as such materials complex well with the boronic acid moieties on the surface of the device. In one embodiment, examples of hydrophilic reactive polymer include diol-terminated polymeric materials such as diol-terminated polyvinyl pyrrolidinone (PVP); diol-terminated polyacrylamides; diol-terminated polyethylene oxides; diol-terminated polyethylene oxide (PEO)/polypropylene oxide (PPO) block copolymers and the like and mixtures thereof. In one embodiment, the hydrophilic reactive polymer is a poly(vinyl alcohol).

In another embodiment, the hydrophilic reactive polymers can be copolymers derived from the polymerization product of ethylenically unsaturated epoxy-containing monomers, such as glycidyl methacrylate, vinylcyclohexyl-1,2-epoxide or glycidyl vinyl carbonate, in which the epoxy group is then hydrolyzed to provide a copolymer units containing 1,2- or 1,3-diols along the backbone of the polymer chain. Such hydrophilic reactive polymers are produced through free radical polymerization techniques known to those skilled in the art.

Generally, the hydrophilic reactive polymers comprise about 1 to about 100 mole percent of reactive monomeric units, more preferably about 5 to about 50 mole percent, most preferably about 10 to about 40 mole percent. The polymers may comprise 0 to about 99 mole percent of non-reactive hydrophilic monomeric units, preferably about 50 to about 95 mole percent, more preferably about 60 to about 90 mole percent (the reactive monomers, once reacted may also be hydrophilic, but are by definition mutually exclusive with the monomers referred to as hydrophilic monomers which are non-reactive). The weight average molecular weight of the hydrophilic reactive polymer may suitably range from about 200 to about 1,000,000, preferably from about 1,000 to about 500,000, and most preferably from about 5,000 to about 100,000.

Suitable hydrophilic non-reactive monomers include aprotic types or protic types or mixtures thereof. Suitable aprotic types include acrylamides such as N,N-dimethylacrylamide, N,N-dimethylmethacrylamide, N-methylmethacrylamide, N-methylacrylamide and the like, but preferably N,N-dimethylacrylamide for increased hydrophilicity; lactams such as N-vinylpyrrolidinone and the like, poly(alkylene oxides) such as methoxypolyoxyethylene methacrylates and the like and mixtures thereof. Suitable protic types include methacrylic acid, hydroxyalkyl(meth)acrylates such as 2-hydroxyethyl methacrylate and the like and mixtures thereof.

If desired, the copolymers may include monomeric units which are hydrophobic optionally may be used in amounts up to 35 mole percent, preferably 0 to 20 mole percent, most preferably 0 to 10 mole percent. Examples of hydrophobic monomers are alkyl methacrylate, fluorinated alkyl methacrylates, long-chain acrylamides such as octyl acrylamide, and the like.

In another embodiment, the hydrophilic reactive polymers can be polymers derived from the polymerization product of an ethylenically unsaturated alkanolamines. Such alkanolamines can be obtained by methods known in the art. Representative examples include those of the general formula $R^{13}$—$N(R^{14}OH)_2$ wherein $R^{13}$ is an ethylenically unsaturated-containing radical as defined herein above; and $R^{14}$ is independently an alkylene group having from one to about six carbon atoms. Suitable ethylenically unsaturated-containing alkanolamines include, but are not limited to, ethylenically unsaturated-containing diethanolamine, ethylenically unsaturated-containing dipropanolamine, ethylenically unsaturated-containing di-isopropanolamine, and the like and mixtures thereof.

In another embodiment, the hydrophilic reactive polymers can be a carboxylic acid-containing polymer or copolymer. Suitable carboxylic acid-containing polymers include, but are not limited to, poly(acrylic acid), poly(methacrylic acid), poly(hyaluronic acid) and the like and mixtures thereof. Suitable carboxylic acid-containing copolymers include, but are not limited to, poly(vinylpyrrolidinone(VP)-co-acrylic acid (AA)), poly(methylvinylether-alt-maleic acid), poly(acrylic acid-graft-ethylene oxide), poly(acrylic acid-co-methacrylic acid), poly(acrylamide-co-AA), poly(AA-co-maleic acid), poly(butadiene-maleic acid) and the like.

In another embodiment, the hydrophilic reactive polymers can be a polyol. Useful polyols include those polyols containing 2 to about 12 carbon atoms and preferably 2 to 4 carbon atoms and from 2 to 8 hydroxyl groups. Representative examples of polyols for use herein include glycerin, ethylene glycol, poly(ethylene glycol), propylene glycol, sorbitol, mannitol, cellulose-containing polymers, monosaccharides, disaccharides, and neutral oligo-polysaccharides, such as from methylcellulose, hydroxypropylmethylcellulose, hydroxypropylguar, and oligomers of poly(vinyl alcohol) and derivatives thereof.

In another embodiment, the hydrophilic reactive polymers can contain ring-opening monomeric units. In one embodiment of the present invention, the ring-opening monomeric units are derived from a ring-opening reactive monomer having an azlactone group represented by the following formula:

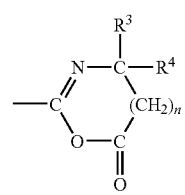

wherein $R^3$ and $R^4$ are independently an alkyl group having 1 to 14 carbon atoms, a cycloalkyl group having 3 to about 14 carbon atoms, an aryl group having 5 to about 12 ring atoms, an arenyl group having 6 to about 26 carbon atoms, and 0 to 3 heteroatoms non-peroxidic selected from S, N, and O, or $R^3$ and $R^4$ taken together with the carbon to which they are joined can form a carbocyclic ring containing 4 to 12 ring atoms, and n is an integer 0 or 1. Such monomeric units are disclosed in U.S. Pat. No. 5,177,165.

The ring structure of such reactive functionalities is susceptible to nucleophilic ring-opening reactions with complementary reactive functional groups on the surface of substrate being treated. For example, the azlactone functionality can react with primary amines, hydroxyl radicals or the like which may be present on the surface of the device to form a covalent bond between the substrate and the hydrophilic reactive polymer at one or more locations along the polymer. A plurality of attachments can form a series of polymer loops on the substrate, wherein each loop comprises a hydrophilic chain attached at both ends to the substrate.

Azlactone-functional monomers for making the hydrophilic reactive polymer can be any monomer, prepolymer, or oligomer comprising an azlactone functionality of the above formula in combination with a vinylic group on an unsaturated hydrocarbon to which the azlactone is attached. Preferably, azlactone-functionality is provided in the hydrophilic polymer by 2-alkenyl azlactone monomers. The 2-alkenyl azlactone monomers are known compounds, their synthesis being described in, for example, U.S. Pat. Nos. 4,304,705; 5,081,197; and 5,091,489, the content of which are incorporated by reference herein. Suitable 2-alkenyl azlactones include, but are not limited to, 2-ethenyl-1,3-oxazolin-5-one, 2-ethenyl-4-methyl-1,3-oxazolin-5-one, 2-isopropenyl-1,3-oxazolin-5-one, 2-isopropenyl-4-methyl-1,3-oxazolin-5-one, 2-ethenyl-4,4-dimethyl-1,3-oxazolin-5-one, 2-isopropenyl-4,-dimethyl-1,3-oxazolin-5-one, 2-ethenyl-4-methyl-ethyl-1,3-oxazolin-5-one, 2-isopropenyl-4-methyl-4-butyl-1,3-oxazolin-5-one, 2-ethenyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-ethenyl-4,4-diethyl-1,3-oxazolin-5-one, 2-ethenyl-4-methyl-4-nonyl-1,3-oxazolin-5-one, 2-isopropenyl-methyl-4-phenyl-1,3-oxazolin-5-one, 2-isopropenyl-4-methyl-4-benzyl-1,3-oxazolin-5-one, and 2-ethenyl-4,4-pentamethylene-1,3-oxazolin-5-one. In a preferred embodiment, the azlactone monomers are represented by the following general formula:

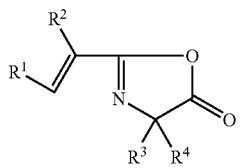

where $R^1$ and $R^2$ independently denote a hydrogen atom or a lower alkyl radical with one to six carbon atoms, and $R^3$ and $R^4$ independently denote alkyl radicals with one to six carbon atoms or a cycloalkyl radical with five or six carbon atoms. Specific examples include 2-isopropenyl-4,4-dimethyl-2-oxazolin-5-one (IPDMO), 2-vinyl-4,4-dimethyl-2-oxazolin-5-one (VDMO), spiro-4'-(2'-isopropenyl-2'-oxazolin-5-one) cyclohexane (IPCO), cyclohexane-spiro-4'-(2'-vinyl-2'-oxazol-5'-one) (VCO), and 2-(-1-propenyl)-4,4-dimethyl-oxazol-5-one (PDMO) and the like. These compounds and their preparation are known in the art, see, e.g., U.S. Pat. No. 6,858,310, the contents of which are incorporated by reference herein.

The azlactone-functional monomers can be copolymerized with hydrophilic and/or hydrophobic comonomers to form hydrophilic reactive polymers. Representative examples of comonomers that can be copolymerized with azlactone functional moieties to form the hydrophilic reactive polymers used to coat a biomedical device include those mentioned above, such as dimethylacrylamide (DMA), hydroxyethyl methacrylate (HEMA), and/or N-vinylpyrrolidone (NVP). Other examples of such comonomers are disclosed in European Patent Publication 0 392 735, the disclosure of which is incorporated by reference. In a preferred embodiment, the hydrophilic reactive polymer is derived from VDMO and DMA is used as a comonomer in order to impart hydrophilicity to the copolymer.

The azlactone-functional monomers can be copolymerized with other monomers in various combinations of weight percentages. Using a monomer of similar reactivity ratio to that of an azlactone monomer will result in a random copolymer. Determination of reactivity ratios for copolymerization are disclosed in Odian, *Principles of Polymerization,* 2nd Ed., John Wiley & Sons, p. 425-430 (1981), the disclosure of which is incorporated by reference herein. Alternatively, use of a comonomer having a higher reactivity to that of an azlactone will tend to result in a block copolymer chain with a higher concentration of azlactone-functionality near the terminus of the chain.

Although not as preferred as monomers, azlactone-functional prepolymers or oligomers having at least one free-radically polymerizable site can also be utilized for providing azlactone-functionality in the hydrophilic reactive polymer according to the present invention. Azlactone-functional oligomers, for example, are prepared by free radical polymerization of azlactone monomers, optionally with comonomers as described in U.S. Pat. Nos. 4,378,411 and 4,695,608, incorporated by reference herein. Representative examples of azlactone-functional oligomers and prepolymers are disclosed in U.S. Pat. Nos. 4,485,236 and 5,081,197 and European Patent Publication 0 392 735, the contents of which are incorporated by reference herein.

The amount of the hydrophilic reactive polymer employed in a packaging solution for storing an ophthalmic device in a packaging system of the present invention is an amount effective to improve the surface properties of the ophthalmic device. Generally, the concentration of the polymer present in the packaging solution of the invention will range from about 0.001 to about 10% w/w and preferably about 0.1 to about 2% w/w.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The packaging solution should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions should be maintained within the range of about 6 to about 9, and preferably about 6.5 to about 7.8. Suitable buffers may be added, such as boric acid, sodium borate, potassium citrate, citric acid, sodium bicarbonate, various mixed phosphate buffers (including combinations of $Na_2HPO_4$, $NaH_2PO_4$ and $KH_2PO4$) and the like and mixtures thereof. Generally, buffers will be used in amounts ranging from about 0.05 to about 2.5 percent by weight, and preferably from about 0.1 to about 1.5 percent by weight of the solution. The packaging solutions of this invention preferably contain a borate buffer, containing one or more of boric acid, sodium borate, potassium tetraborate, potassium metaborate or mixtures of the same.

Typically, the solutions of the present invention are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to, sodium and potassium chloride, dextrose, glycerin, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, preferably from about 200 to about 400 mOsm/kg, more preferably from about 250 to about 350 mOsm/kg, and most preferably from about 280 to about 320 mOsm/kg.

If desired, one or more additional components can be included in the packaging solution. Such additional component or components are chosen to impart or provide at least one beneficial or desired property to the packaging solution. Such additional components may be selected from components which are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetraacetate, alkali metal hexametaphosphate, citric acid, sodium citrate and the like and mixtures thereof.

Useful viscosity builders include, but are not limited to, hydroxyethyl cellulose, hydroxymethyl cellulose, polyvinyl pyrrolidone, polyvinyl alcohol and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing an ophthalmic device such as a contact lens according to the present invention includes at least packaging an ophthalmic device immersed in the aqueous packaging solution described above. The method may include immersing the ophthalmic device in an aqueous packaging solution prior to delivery to the customer/wearer, directly following manufacture of the contact lens. Alternately, the packaging and storing in the solution of the present invention may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution according to the present invention.

In one embodiment, the steps leading to the present ophthalmic device packaging system includes (1) molding an ophthalmic device in a mold comprising at least a first and second mold portion, (2) hydrating and cleaning the device in a container comprising at least one of the mold portions, (3) introducing the packaging solution with the copolymer into the container with the device supported therein, and (4) sealing the container. Preferably, the method also includes the step of sterilizing the contents of the container. Sterilization may take place prior to, or most conveniently after, sealing of the container and may be effected by any suitable method known in the art, e.g., by autoclaving of the sealed container at temperatures of about 120° C. or higher.

The following examples are provided to enable one skilled in the art to practice the invention and are merely illustrative of the invention. The examples should not be read as limiting the scope of the invention as defined in the claims.

In the example, the following abbreviations are used.
TRIS: tris(trimethylsiloxy)silylpropyl methacrylate
NVP: N-vinyl-2-pyrrolidone
HEMA: 2-hydroxyethyl methacrylate
HEMAVC: methacryloxyethyl vinyl carbonate
Vazo™ 64: a thermal polymerization initiator, said to be 2,2'-azobisisobutyronitrile (DuPont Chemicals, Wilmington, Del.)
IMVT: 1,4-bis(4-(2-methacryloxyethyl)phenylamino)anthraquinone
DMA: dimethylacrylamide
VDMO: 2-vinyl-4,4-dimethyl-2-oxazolin-5-one

EXAMPLE 1

Preparation of a Contact Lens

Mixtures were made by mixing the following components listed in Table 1, at amounts per weight.

TABLE 1

| Ingredient | Weight Percent |
|---|---|
| Polyurethane-siloxane prepolymer | 53 |
| TRIS | 15 |
| NVP | 33 |
| HEMA | 5 |
| HEMAVC | 1 |
| Boronic acid monomer | 1 |
| N-hexanol | 15 |
| Vazo-64 | 0.5 |
| IMVT | 150 ppm |

The resulting mixture is cast into contact lenses by introducing the mixture to a mold assembly composed of an ethyl vinyl alcohol mold for the anterior surface and an ethyl vinyl alcohol mold for the posterior surface and thermally curing the mixture at 100° C. for 2 hours. The resulting contact lens is released from the mold, extracted with isopropyl alcohol for 4 hours and placed in a buffer solution. The boronic acid monomer used in this example is of the formula:

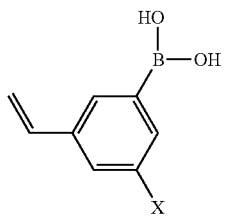

wherein X is —$NO_2$.

EXAMPLE 2

The lenses of Example 1 are placed in polypropylene contact lens blister packs containing a buffered saline solution containing 1% by weight of a copolymer of DMA/VDMO. The blisters are sealed and autoclaved for one cycle.

EXAMPLE 3

The lenses of Example 1 are placed in polypropylene contact lens blister packs containing a buffered saline solution containing 1% by weight of a copolymer of vinylalcohol and vinylpyrrolidone. The blisters are sealed and autoclaved for one cycle.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method of preparing a package comprising a storable, sterile ophthalmic device, the method comprising:
   (a) providing an ophthalmic device obtained from a polymerization product of a monomeric mixture comprising (i) a polymerizable monomer containing a boronic acid moiety and an electron withdrawing moiety; and (ii) an ophthalmic device-forming comonomer;
   (b) immersing the ophthalmic device in an aqueous packaging solution comprising a hydrophilic reactive polymer having complementary reactive functionalities aloneg the polymer chain, wherein the solution has an osmolality of at least about 200 mOsm/kg and a pH in the range of about 6 to about 9;
   (c) packaging the solution and the ophthalmic device in a manner preventing contamination of the device by microorganisms; and
   (d) sterilizing the packaged solution and ophthalmic device wherein the hydrophilic reactive polymer is a copolymer derived from 2-vinyl-4,4-dimethyl-2-oxazolin-5-one and dimethylacrylamide.

2. A method of preparing a package comprising a storable, sterile ophthalmic device, the method comprising:
   (a) providing an ophthalmic device obtained from a polymerization product of a monomeric mixture comprising (i) a polymerizable monomer containing a boronic acid moiety and an electron withdrawing moiety; and (ii) an ophthalmic device-forming comonomer;
   (b) immersing the ophthalmic device in an aqueous packaging solution comprising a hydrophilic reactive polymer having complementary reactive functionalities along the polymer chain, wherein the solution has an osmolality of at least about 200 mOsm/k and a pH in the range of about 6 to about 9;
   (c) packaging the solution and the ophthalmic device in a manner preventing contamination of the device by microorganisms; and
   (d) sterilizing the packaged solution and ophthalmic device wherein the hydrophilic reactive polymer is selected from the group consisting of glycerol (meth)acrylate, erythritol (meth) acrylate, xylitol (meth)acrylate, sorbitol (meth)acrylate and mixtures thereof.

3. A method of preparing a package comprising a storable, sterile ophthalmic device, the method comprising:
   (a) providing an ophthalmic device obtained from a polymerization product of a monomeric mixture comprising (i) a polymerizable monomer containing a boronic acid moiety and an electron withdrawing moiety; and (ii) an ophthalmic device-forming comonomer;
   (b) immersing the ophthalmic device in an aqueous packaging solution comprising a hydrophilic reactive polymer having complementary reactive functionalities along the polymer chain, wherein the solution has an osmolality of at least about 200 mOsm/kg and a pH in the range of about 6 to about 9;
   (c) packaging the solution and the ophthalmic device in a manner preventing contamination of the device by microorganisms; and
   (d) sterilizing the packaged solution and ophthalmic device wherein the hydrophilic reactive polymer comprises monomeric units of glyceryl (meth)acrylate and monomeric units of (meth)acrylic acid.

4. A method of preparing a package comprising a storable, sterile ophthalmic device, the method comprising:
   (a) providing an ophthalmic device obtained from a polymerization product of a monomeric mixture comprising (i) a polymerizable monomer containing a boronic acid moiety and an electron withdrawing moiety; and (ii) an ophthalmic device-forming comonomer;
   (b) immersing the ophthalmic device in an aqueous packaging solution comprising a hydrophilic reactive polymer having complementary reactive functionalities along the polymer chain, wherein the solution has an osmolality of at least about 200 mOsm/kg and a pH in the range of about 6 to about 9;
   (c) packaging the solution and the ophthalmic device in a manner preventing contamination of the device by microorganisms; and
   (d) sterilizing the packaged solution and ophthalmic device wherein the hydrophilic reactive polymer comprises monomeric units of vinyl alcohol and monomeric units of vinylpyrrolidone.

* * * * *